United States Patent [19]
Nakano et al.

[11] Patent Number: 5,629,180
[45] Date of Patent: May 13, 1997

[54] PROCESS FOR PRODUCING L-AMINO ACID

[75] Inventors: Tetsuo Nakano, Machida; Motokazu Nakayama, Ami-machi; Mariko Shitashige, Tokuyama; Masato Ikeda, Hofu, all of Japan; Satoru Furukawa, Chesterfield, Mo.

[73] Assignee: Kyowa Hakko Kogyo Co., Ltd., Tokyo, Japan

[21] Appl. No.: 496,098

[22] Filed: Jun. 28, 1995

[30] Foreign Application Priority Data

Jun. 30, 1994 [JP] Japan .................................. 6-149680

[51] Int. Cl.$^6$ .......................... C12P 13/04; C12P 13/06; C12P 13/08; C12N 1/20
[52] U.S. Cl. ........................ 435/106; 435/115; 435/116
[58] Field of Search .................................. 435/106, 116, 435/115, 252.8

[56] References Cited

FOREIGN PATENT DOCUMENTS

| | | |
|---|---|---|
| 0030727 | 6/1981 | European Pat. Off. . |
| 0542487 | 5/1993 | European Pat. Off. . |
| 0557996 | 9/1993 | European Pat. Off. . |
| 56-51989 | 5/1981 | Japan . |
| 56-72695 | 6/1981 | Japan . |
| 4-94692 | 3/1992 | Japan . |
| 4-88991 | 3/1992 | Japan . |

OTHER PUBLICATIONS

Patent Abstracts of Japan, Unexamined Applications, vol. 2, No. 105; Aug. 30, 1978.
Patent Abstracts of Japan, Unexamined Applications, vol. 5, No. 114; Jul. 23, 1981.
Biosci. Biotech. Biochem. 57, 51–55, 1993, I. Shiio, et al.

*Primary Examiner*—Herbert J. Lilling
*Attorney, Agent, or Firm*—Antonelli, Terry, Stout & Kraus, LLP

[57] ABSTRACT

Disclosed is a process for producing an L-amino acid which comprises culturing a microorganism belonging to the genus *Escherichia*, having resistance to 2-ketobutyric acid and ability to produce the L-amino acid in a medium until the L-amino acid is accumulated in the medium, and recovering the L-amino acid therefrom.

2 Claims, No Drawings

PROCESS FOR PRODUCING L-AMINO ACID

BACKGROUND OF THE INVENTION

The present invention relates to a process for producing an L-amino acid by fermentation. An aliphatic amino acid such as L-valine, L-leucine and L-isoleucine is an essential nutrient for humans and animals, and is employed in pharmaceuticals, foods and animal feeds.

Various processes for producing an L-amino acid by direct fermentation are known. As a process for producing L-valine, processes using microorganisms belonging to the genus *Serratia*, *Corynebacterium* and *Arthrobacter* are known. As a process for producing L-valine using a microorganism belonging to the genus *Escherichia*, a process using a microorganism having resistant to β-hydroxyisoleucine, β-2-thienylalanine or 1,2,4-triazolalanine is known (Japanese Published Unexamined Patent Application No. 51989/81).

As a process for producing L-leucine, processes using microorganisms belonging to the genus *Serratia*, *Corynebacterium* and *Arthrobactor* are known. As a process for producing L-leucine using a microorganism belonging to the genus *Escherichia*, a process using a microorganism having resistance to β-2-thienylalanine is known (Japanese Published Unexamined Patent Application No. 72695/81). As a process for producing L-isoleucine, processes using microorganisms of *Serratia*, *Corynebacterium* and *Arthrobactor* are known. As a process for producing L-isoleucine using a microorganism belonging to the genus *Escherichia*, a process using a microorganism having resistance to isoleucine analogues is known (EP-A-0542487).

However, there has not been known a process for producing aliphatic amino acids using microorganisms having resistance to 2-ketobutyric acid.

SUMMARY OF THE INVENTION

An object of the present invention is to provide an industrially efficient process for producing an L-amino acid useful in pharmaceuticals, foods and animal feeds.

According to the present invention, provided is a process for producing an L-amino acid which comprises culturing, in a medium, a microorganism belonging to the genus *Escherichia*, having resistance to 2-ketobutyric acid and having ability of producing the L-amino acid until the L-amino acid is accumulated in the medium, and recovering the L-amino acid therefrom.

DETAILED DESCRIPTION OF THE INVENTION

In the present invention, any microorganism can be used, so long as it belongs to the genus *Escherichia*, has resistance to 2-ketobutyric acid and has ability to produce an L-amino acid.

An example of an L-amino acid according to the present invention is an aliphatic amino acid, preferably, L-valine, L-leucine and L-isoleucine.

An L-amino acid-producing microorganism according to the present invention can be obtained by subjecting a microorganism belonging to the genus *Escherichia* and having ability to produce an L-amino acid to a conventional mutation treatment such as treatment with N-methyl-N'-nitro-N-nitrosoguanidine and X-ray irradiation, spreading the resulting microorganisms on a minimum medium containing 2-ketobutyric acid, and picking up colonies grown on the minimum medium. A microorganism used in the present invention may also be obtained by endowing a microorganism belonging to the genus *Escherichia* and having resistance to 2-ketobutyric acid, which is derived from a wild strain, with nutrient auxotrophy, L-amino acid metabolism antagonist-resistance, etc. for improving L-amino acid productivity. Preferred examples of the suitable microorganism are *Escherichia coli* H-9069, H-9071 and H-9073.

In the production of an L-amino acid using a microorganism of the present invention, any conventional method for culturing bacteria is applicable. As a medium for the culture, any of a synthetic medium and a natural medium may be used so long as it suitably contains carbon sources, nitrogen sources, inorganic substances and other nutrients required for the microorganism used.

As the carbon sources, carbohydrates such as glucose, fructose, lactose, molasses, cellulose hydrolysates, hydrolysate of crude sugar and starch hydrolysate, organic acids such as pyruvic acid, acetic acid, fumaric acid, malic acid and lactic acid, and alcohols such as glycerin and ethanol, etc. can be used.

As the nitrogen sources, ammonia and ammonium salt of inorganic or organic acids, such as ammonium chloride, ammonium sulfate, ammonium acetate, and ammonium phosphate, amines, peptone, meat extract, corn steep liquor, casein hydrolysate, soybean cake hydrolysate, various cultured cells and their digested products can be used.

As the inorganic substances, potassium dihydrogen phosphate, dipotassium hydrogen phosphate, magnesium phosphate, magnesium sulfate, magnesium chloride, sodium chloride, ferrous sulfate, manganese sulfate, copper sulfate, calcium chloride and calcium carbonate may be used.

Culturing is carried out under aerobic condition, for example, by shaking culture, agitation submerged culture, etc. at a temperature of 20° to 40° C., preferably 28° to 37° C. The pH of the medium is kept within the range of 5 to 9, preferably around neutral pH. The pH of the medium is adjusted with calcium carbonate, inorganic or organic acids, alkaline solutions, ammonia, pH buffer agents, and the like. Usually, after culturing for 1 to 7 days, an L-amino acid is accumulated in the culture.

After completion of the culturing, precipitates such as cells are removed from the culture by means of centrifugation, etc. By using ion exchange treatment, concentration, salting out, etc. in combination, an L-amino acid can be recovered from the culture. Examples of the present invention are described below.

EXAMPLE 1

Preparation of L-valine-producing Mutant Having Resistance to 2-ketobutyric Acid

*Escherichia coli* H-9068 (a methionine and diaminopimelic acid non-auxotrophic strain derived through spontaneous reverse mutation from methionine and diaminopimelic acid auxotrophic strain *Escherichia coli* ATCC 21530) was subjected to a conventional mutation treatment with N-methyl-N'-nitro-N-nitrosoguanidine (0.5 mg/ml, 33° C., 30 minutes) and then spread on a minimum agar plate (0.5% glucose, 0.2% ammonium chloride, 0.3% potassium dihydrogenphosphate, 0.6% disodium hydrogenphosphate, 0.01% magnesium sulfate, 20 mg/L calcium chloride, 2% agar, pH 7.2) containing 10 g/L disodium 2-ketobutyrate. After culturing at 33° C. for 2 to 5 days, larger colonies grown were picked up as the strains having resistance to 2-ketobutyric acid and subjected to the L-valine production test. Strains having L-valine-productivity greater than that of the parent strain were obtained at a frequency of about 20%. Among these mutants, the strain having the highest L-valine productivity was designated as *Escherichia coli* H-9069. H-9069 strain was deposited with the National Institute of Bioscience and Human-Technology, Agency of Industrial Science and Technology, Japan on Jun. 21, 1994 under the Budapest Treaty with an accession number FERM BP-4705.

EXAMPLE 2

Preparation of L-leucine-producing Mutant Having Resistance to 2-ketobutyric Acid In the same manner as in Example 1 except for using *Escherichia coli* H-9070 (a mutant strain having resistance to 4-azaleucine derived from H-9068 strain) instead of *Escherichia coli* H-9068, the strain was subjected to the mutation treatment and then cultured on the minimum agar plate containing 10 g/L disodium 2-ketobutyrate. After culturing, larger colonies grown were picked up as the strains having resistance to 2-ketobutyric acid and subjected to the L-leucine production test. Strains having L-leucine-productivity greater than that of the parent strain were obtained at a frequency of about 20%. Among these mutants, the strain having the highest L-leucine productivity was designated as *Escherichia coli* H-9071. H-9070 strain used as the parent strain and H-9071 strain having resistance to 2-ketobutyric acid derived therefrom were deposited with the National Institute of Bioscience and Human-Technology, Agency of Industrial Science and Technology, Japan on Jun. 21, 1994 under the Budapest Treaty with accession numbers FERM BP-4704 and FERM BP-4703, respectively.

EXAMPLE 3

Preparation of L-isoleucine-producing Mutant Having Resistance to 2-ketobutyric Acid In the same manner as in Example 1 except that *Escherichia coli* H-8683 (FERM BP-4052: a methionine-auxotrophic α-strain having resistance to rifampicin, α-amino-β-hydroxyvaleric acid, thioisoleucine, arginine hydroxamate, DL-ethionine, S-(2-aminoethyl)-L-cysteine and D-serine) was used instead of *Escherichia coli* H-9068, the concentration of disodium 2-ketobutyrate in the minimum agar plate was 5 g/L instead of 10 g/L and that 0.1 g/L DL-methionine was added to the minimum agar plate, the strain was subjected to the mutation treatment and then cultured. After culturing, larger colonies grown were picked up as the strains having resistance to 2-ketobutyric acid and subjected to the L-isoleucine production test. The strains having L-isoleucine-productivity greater than that of the parent strain were obtained at a frequency of about 5%. Among these mutants, the strain having the highest L-isoleucine productivity was designated as *Escherichia coli* H-9073. H-9073 strain was deposited with the National Institute of Bioscience and Human-Technology, Agency of Industrial Science and Technology, Japan on Jun. 21, 1994 under the Budapest Treaty with an accession number FERM BP-4707.

EXAMPLE 4

Comparison of Degree of Resistance to 2-ketobutyric Acid

The degrees of resistance to 2-ketobutyric acid of the mutants obtained in Examples 1 to 3, namely, mutant strains H-9069, H-9071 and H-9073 were compared with those of the parent strains thereof, namely, H-9068, H-9070 and H-8683, respectively. Each of the above-mentioned strains was inoculated into a natural medium (1% tripton, 0.5% yeast extract, 1% NaCl, pH 7.2) and cultured with shaking for 24 hours. The resulting culture was diluted with sterilized water and spread onto the minimum agar plate containing disodium 2-ketobutyrate at the concentration as shown in Table 1 and 0.1 g/L DL-methionine at a density of $1 \times 10^3$ cells/cm². Culturing was carried out at 33° C. for 72 hours. After completion of the culturing, the degree of resistance to 2-ketobutyric acid of the strain was determined on the basis of its growth. The results are shown in Table 1. The degrees of resistance of mutant strains H-9069, H-9071 and H-9073 were higher than those of the parent strains thereof, respectively.

TABLE 1

| Strain | Concentration of disodium 2-ketobutyrate (g/L) | | | |
|---|---|---|---|---|
| | 0 | 3 | 5 | 10 |
| H-9068 | + | + | − | − |
| H-9069 | + | + | + | + |
| H-9070 | + | + | − | − |
| H-9071 | + | + | + | + |
| H-8683 | + | + | − | − |
| H-9073 | + | + | + | − |

+: sufficient growth,
−: no growth

EXAMPLE 5

Production Tests of L-valine, L-leucine and L-isoleucine

Production tests of L-valine, L-leucine and L-isoleucine were carried out by culturing mutant strains obtained in Examples 1 to 3. Each of *Escherichia coli* H-9068, H-9069, H-9070, H-9071, H-8683 and H-9073 was inoculated onto 20 ml of seed medium (2% glucose, 1% peptone, 1% yeast extract, 0.25% NaCl, pH 7.0) in a 300 ml conical flask and cultured with shaking at 30° C. for 16 hours. 2 ml of the resulting seed culture was transferred to 2 L conical flask containing 250 ml of production medium (6% glucose, 0.2% corn steep liquor, 1.6% ammonium sulfate, 0.1% potassium phosphate, 100 mg/L DL-methionine, 4% magnesium phosphate, 1% calcium carbonate, pH 7.0), and culturing was carried out at 30° C. for 72 hours with shaking. After the completion of the culturing, the amount of each of L-valine, L-leucine and L-isoleucine accumulated was quantitatively determined by high-pressure liquid chromatography. The results are shown in Table 2.

TABLE 2

| Strain | Accumulated L-amino acid (g/L) | | |
|---|---|---|---|
| | L-valine | L-leucine | L-isoleucine |
| H-9068 | 8.0 | | |
| H-9069 | 9.5 | | |
| H-9070 | | 3.4 | |
| H-9071 | | 5.0 | |
| H-8683 | | | 14.1 |
| H-9073 | | | 15.0 |

One liter of each of L-amino acids containing cultures obtained by culturing a mutant strain selected from H-9069, H-9071 and H-9073 was centrifuged (3000 rpm, 10 minutes)

to remove the cells and other impurities therefrom. The supernatant obtained was passed through a column packed with strong acid cationic exchange resin DIAION (type H⁺; product of Mitsubishi Chemical Corporation, Japan) to adsorb the L-amino acid thereon. The column was washed with water, and subjected to elution with 0.5N aqueous ammonia to collect the L-amino acid fractions. The collected fractions were concentrated and ethanol was added to the concentrate. By storing the mixture under cooling, 6.8 g of L-valine crystal having purity of 98% or higher was obtained from one liter of the L-valine-containing culture obtained by culturing H-9069 strain, 3.8 g of L-leucine crystal having purity of 98% or higher was obtained from one liter of the L-leucine-containing culture obtained by culturing H-9071 strain and 12.6 g of L-isoleucine crystal having purity of 98% or higher was obtained from one liter of the L-isoleucine-containing culture obtained by culturing H-9073 strain.

According to the present invention, an L-amino acid can be produced industrially at a high efficiency.

What is claimed is:

1. A process for producing an L-amino acid which comprises culturing a microorganism selected from the group consisting of *Escherichia coli* H-9069, H-9071 and H-9073, having resistance to 2-ketobutyric acid and having ability to produce the L-amino acid in a medium until the L-amino acid is accumulated in the medium, and recovering the L-amino acid therefrom, wherein said L-amino acid is an aliphatic amino acid selected from the group consisting of L-valine, L-leucine and L-isoleucine.

2. A process for producing an L-amino acid which comprises culturing a microorganism belonging to the genus *Escherichia*, having resistance to 5 g/l of 2-ketobutyric acid and having ability to produce the L-amino acid in a medium until the L-amino acid is accumulated in the medium, and recovering the L-amino acid therefrom, wherein said L-amino acid is an aliphatic amino acid selected from the group consisting of L-valine, L-leucine and L-isoleucine.

* * * * *